United States Patent
Edwards et al.

(10) Patent No.: US 9,169,399 B2
(45) Date of Patent: Oct. 27, 2015

(54) METHOD OF CHARACTERISING A SCATTERING COLOURED PIGMENT

(75) Inventors: John Lalande Edwards, Durham (GB); Karl Lowry, Stockton-on-Tees (GB); Emily Ruth Parnham, Stockton-on-Tees (GB); Sean Oliver Edward Reid, Ashbourne (GB); John Robb, Stockton-on-Tees (GB); Rebecca Louise Tonkin, Stockton-on-Tees (GB)

(73) Assignee: TIOXIDE EUROPE LIMITED, Wynyard Park (GB)

( * ) Notice: Subject to any disclaimer, the term of this patent is extended or adjusted under 35 U.S.C. 154(b) by 0 days.

(21) Appl. No.: 13/638,120

(22) PCT Filed: Mar. 25, 2011

(86) PCT No.: PCT/GB2011/050619
§ 371 (c)(1),
(2), (4) Date: Sep. 28, 2012

(87) PCT Pub. No.: WO2011/121339
PCT Pub. Date: Oct. 6, 2011

(65) Prior Publication Data
US 2013/0016339 A1  Jan. 17, 2013

(30) Foreign Application Priority Data
Mar. 30, 2010 (GB) .................................. 1005344.5

(51) Int. Cl.
*G01J 3/00* (2006.01)
*C09C 1/00* (2006.01)
(Continued)

(52) U.S. Cl.
CPC .............. *C09C 1/0084* (2013.01); *C09D 7/007* (2013.01); *G01N 21/25* (2013.01);
(Continued)

(58) Field of Classification Search
CPC .. G01N 21/314; G02B 6/0018; G02B 6/0028; G02B 6/0068; G02B 6/0076; G02B 6/002; G02B 6/006; G02B 6/003; G02B 6/0088; G02B 6/0036; G02B 27/0101; G02B 6/005; G02B 6/0065; G02B 27/017; G02B 6/0078
USPC .......................................................... 356/51
See application file for complete search history.

(56) References Cited

U.S. PATENT DOCUMENTS 5,272,518 A * 12/1993 Vincent .......................... 356/405
6,362,885 B1 * 3/2002 Osumi et al. .................. 356/402
(Continued)

FOREIGN PATENT DOCUMENTS

EP      1 580 166        9/2005
JP   Hei 10-310727 A   11/1998
(Continued)

OTHER PUBLICATIONS

Levinson, Ronnen, et al., "Solar spectral optical properties of pigments—Part I : Model for deriving scattering and absorption coefficients from transmittance and reflectance measurements", *Solar Energy Materials & Solar Cells* 89 (2005) 319-349.

*Primary Examiner* — Michael P Stafira
(74) *Attorney, Agent, or Firm* — Monique M. Raub

(57) ABSTRACT

The invention provides a method of characterizing a scattering colored pigment for use in the determination of the absorption and scattering coefficients of the scattering colored pigment, the method comprising the step of obtaining a reflectance spectrum of a mixture of the scattering colored pigment with a substantially non-absorbing scattering pigment at a plurality of different volume fractions wherein the substantially non-absorbing scattering pigment has a particle size greater than 0.6 micron. Also provided is a pigment characterization system adapted to perform the method of the invention to characterize a scattering colored pigment.

18 Claims, 4 Drawing Sheets

(51) Int. Cl.
 *C09D 7/00* (2006.01)
 *G01N 21/25* (2006.01)
 *G01J 3/46* (2006.01)

(52) U.S. Cl.
 CPC ........ *C01P 2004/61* (2013.01); *C01P 2006/60* (2013.01); *C01P 2006/62* (2013.01); *C01P 2006/63* (2013.01); *C01P 2006/64* (2013.01); *G01J 3/463* (2013.01)

(56) References Cited

U.S. PATENT DOCUMENTS

| | | | |
|---|---|---|---|
| 2002/0149770 A1* | 10/2002 | Kubo et al. | 356/402 |
| 2005/0126441 A1 | 6/2005 | Skelhorn | |
| 2006/0181707 A1* | 8/2006 | Gibson et al. | 356/402 |
| 2008/0241472 A1 | 10/2008 | Shiao et al. | |
| 2009/0196819 A1 | 8/2009 | Asakura | |
| 2011/0041726 A1 | 2/2011 | Robb et al. | |
| 2011/0286000 A1* | 11/2011 | Hu et al. | 356/445 |

FOREIGN PATENT DOCUMENTS

| | | |
|---|---|---|
| JP | Hei 11-326054 A | 11/1999 |
| JP | 2003-160757 A | 6/2003 |
| JP | 2003-226830 A | 8/2003 |
| WO | WO 2009/136141 A | 11/2009 |

* cited by examiner

METHOD OF CHARACTERISING A SCATTERING COLOURED PIGMENT

CROSS-REFERENCE TO RELATED APPLICATIONS

This application is the National Phase of International Application PCT/GB2011/050619 filed Mar. 25, 2011 which designated the U.S. and which claims priority to Great Britain App. Serial No. 1005344.5 filed Mar. 30, 2010. The noted applications are incorporated herein by reference.

FIELD OF THE INVENTION

This invention relates to a method of characterising a scattering coloured pigment for use in the determination of the absorption and scattering coefficients of the scattering coloured pigment. It also relates to a method of colour matching and, in particular, to a colour matching method for coloured pigment mixtures. This invention also relates to a pigment characterisation system for performing the method.

BACKGROUND TO THE INVENTION

Paints typically comprise pigments dispersed within a binder. The pigments may comprise i) weakly scattering or substantially non-scattering coloured pigments that substantially do not scatter light and selectively absorb different wavelengths of visible light to impart colour ii) substantially non-absorbing pigments that scatter light and iii) strongly scattering coloured pigments that scatter light and selectively absorb different wavelengths of visible light to impart colour.

The Kubelka Munk equation is a radiation transfer equation commonly used in the field of paints and pigments to characterise the visible reflection spectrum of materials. The use of the Kubelka Munk method when describing multi-component pigment mixtures is usually based on equations of the form:

$$\left(\frac{K}{S}\right) = \frac{k_1 \times \varphi_1 + k_2 \times \varphi_2 + k_3 \times \varphi_3 \ldots}{s_1 \times \varphi_1 + s_2 \times \varphi_2 + s_3 \times \varphi_3 \ldots}$$

where (K/S) is the ratio of the Kubelka Munk absorption and scattering coefficients and $k_i$, $s_i$ and $\varphi_i$ are the absorption coefficient, scattering coefficient and volume fraction for an individual pigment. The above equation is inaccurate and problematic at high volume fractions of scattering pigments due to crowding effects (for example, for conventional titanium dioxide pigments, in the visible part of the spectrum, inaccuracies are apparent at pigment volume concentrations greater than about 15%). Crowding effects reduce the scattering efficiency of a scattering pigment due to a high density of pigment particles in a particular volume, thus the relationship between scattering efficiency and pigment volume concentration becomes non linear.

The particle volume concentration at which crowding effects occur is different for different pigments and different wavelengths. As the particle size of the pigment increases or wavelength decreases, the volume fraction above which the crowding effect takes effect is increased. Thus, when considering the near infrared part of the spectrum, the pigment volume concentration below which the relationship between scattering efficiency and pigment volume concentration is linear, occurs at even lower pigment volume concentrations than when considering the visible part of the spectrum.

One traditional approach to characterising the absorption and scattering coefficients of a pigment in the visible part of the spectrum is to measure reflectivity when incorporated into carbon black and titanium dioxide pigment pastes. The extension of this approach into the near infrared part of the spectrum is problematic, especially for pigments where both scattering and absorption are significant. The opacity of a conventional titanium dioxide paste falls rapidly as the wavelengths of interest are increased into the near infrared.

To obtain an optically thick system in the near infrared using conventional paint film thicknesses (<300 nm) thus requires volume fractions of pigment above which the crowding effect needs to be taken account of. At such volume fractions the addition of a significant volume fraction of a second scattering particle will lead to a more complex relationship between the Kubelka Munk scattering coefficient S and the volume fraction of the second scattering particle $\varphi_2$ than that when crowding effects can be ignored.

$$S \neq \varphi_1 s_1 + \varphi_2 s_s$$

$$S = S(\varphi_1, \varphi_2)$$

SUMMARY OF THE INVENTION

According to a first aspect of the invention, we provide a method of characterising a scattering coloured pigment for use in the determination of the absorption and scattering coefficients of the scattering coloured pigment, the method comprising the steps of:
i) obtaining a reflectance spectrum of a mixture of the scattering coloured pigment with a substantially non-absorbing scattering pigment at a plurality of different volume fractions wherein the substantially non-absorbing scattering pigment has a particle size >0.6 micron.

This method is advantageous as the characterisation by the reflectance spectrum using large particle size non-absorbing scattering pigment allows accurate characterisation due to the reduction of crowding effects. Certain scattering coloured pigments such as Complex Inorganic Coloured Pigments (CICPs), nickel antimony titanate or chromium antimony titanate have particle sizes that are much larger than those of conventional titanium dioxide pigments. This presents problems in the characterisation of the scattering coloured pigment. For example, the particle size of CICP titanates is typically 0.6-1.3 micron and the particle size of conventional titanium dioxide pigments is 0.2-0.3 micron. However, by using a larger crystal size titanium dioxide particle (>0.6 micron) rather than conventional titanium dioxide pigment in the white paste mixture, the scattering and absorption coefficients of such "large particle size" scattering coloured pigments can be better characterised through the visible and near infrared parts of the spectrum. Optically thick paint films can be formulated at volume fractions of the large crystal titanium dioxide and "large particle size" scattering coloured pigments at which crowding effects do not have a substantial effect. Using this approach the subsequently calculated scattering coefficient and absorption coefficient values can be accurately determined and used to match colours and their total solar reflections can be predicted.

A method which may be used for determining the particle size of the pigment particles is X-ray sedimentation.

Absorption coefficients and scattering coefficients that define the extent to which a pigment respectively absorbs and scatters light over the electromagnetic spectrum are known and may be determined by methods well known to those skilled in the art, for example, such as those described in "Solar Spectral Optical Properties of Pigments—Part I: Model for Deriving Scattering and Absorption Coefficients From Transmittance and Reflectance Measurements", R Levinson et al., Solar Energy Materials and Solar Cells 89 (2005) 319-349, the entire contents of which is incorporated herein by reference.

A pigment that is substantially non-absorbing may have an average absorption coefficient in the visible region of the electromagnetic spectrum (i.e. in the region of 400 am to 760 nm) of less than 50 mm$^{-1}$, e.g. less than 30 mm$^{-1}$, or less than 10 mm$^{-1}$.

A pigment that is scattering may have a maximum scattering coefficient in the visible and near infrared region of the electromagnetic spectrum (i.e. in the region of 400 nm to 3000 nm, e.g. in the region of 400 nm to 2500 nm) of 50 mm$^{-1}$ or more, e.g. 75 mm$^{-1}$ or more, or 100 mm$^{-1}$ or more.

Preferably the method includes the step of ii) obtaining a scattering coefficient of the substantially non-absorbing scattering pigment as a function of volume fraction and wavelength.

Preferably the method includes the step of determining the particle size of the scattering coloured pigment and selecting a non-absorbing scattering pigment having a particle size within 0.5 microns, and most preferably within 0.2 microns, of the particle size of the scattering coloured pigment for performing characterisation therewith. This is advantageous as the effects of crowding are reduced, which results in an improved characterisation of the coloured pigment, which can then be used to accurately colour match and for calculating the total solar reflection.

The substantially non-absorbing scattering pigment has a particle size of approximately 0.6 microns or more (such as greater than 0.7 microns, greater than 0.8 microns, greater than 0.9 microns, greater than 1 micron, greater than 1.1 microns, greater than 1.2 microns, greater than 1.3 microns or greater than 1.4 microns). The particle size may in one embodiment be greater than 0.6 microns and up to 2 microns, or greater than 0.6 microns and up to 1.5 microns, or greater than 0.6 microns and up to 1.4 microns.

Preferably, the substantially non-absorbing scattering pigment comprises a large particle size titanium dioxide pigment. A conventional titanium dioxide pigment has a particle size between 0.2 and 0.3 microns. Thus, a large particle size titanium dioxide pigment has a particle size greater than this, at approximately 0.6 microns or more (such as greater than 0.7 microns, greater than 0.8 microns, greater than 0.9 microns, greater than 1 micron, greater than 1.1 microns, greater than 1.2 microns, greater than 1.3 microns or greater than 1.4 microns). The titanium dioxide particle size may in one embodiment be greater than 0.6 microns and up to 2 microns, or greater than 0.6 microns and up to 1.5 microns, or greater than 0.6 microns and up to 1.4 microns.

Preferably the scattering coloured pigment is a large particle size pigment having a particle size of greater than 0.6 microns (such as greater than 0.7 microns, greater than 0.8 microns, greater than 0.9 microns, greater than 1 micron, greater than 1.1 microns, greater than 1.2 microns, greater than 1.3 microns or greater than 1.4 microns), for example greater than 0.6 microns and up to 1.5 microns or greater than 0.6 microns and up to 1.4 microns; typically the scattering coloured pigment is a large particle size pigment having a particle size of 0.6 to 1.3 microns.

Preferably the scattering coloured pigment is selected from: Complex Inorganic Coloured Pigments; Nickel Antimony Titanate; Chrome Antimony Titanate; Manganese Antimony Titanate; Zinc Iron Chromite Brown Spinel; Chromium Green-Black Hematite; Cobalt Aluminate Blue Spinel; Cobalt Titanate Green Spinel; and Cobalt Chromite Green Spinel.

This method is particularly suited to the accurate characterisation of large particle size pigments, as the crowding effects are reduced by the use of a large particle size substantially non-absorbing scattering pigment (e.g. TiO$_2$). This is advantageous as the particle size of the scattering coloured pigment is comparable with the size of the particles of the non-absorbing scattering pigment. This has been found to allow accurate characterisation of the scattering coloured pigment over a broad range of wavelengths, particularly over the near infrared wavelengths, as the effect of crowding is reduced.

Preferably the reflectance spectrum of the scattering coloured pigment is determined at least over wavelengths in the visible spectrum and infra-red and most preferably over a wavelength range of 300 nm to 2500 nm.

Preferably the method includes the steps of:
iii) obtaining an absorption coefficient of a weakly scattering black pigment as a function of wavelength at a plurality of different volume fractions; and
iv) obtaining a further reflectance spectrum of a mixture of the scattering coloured pigment with the black pigment at a plurality of different volume fractions.

A weakly scattering pigment may be one that has a maximum scattering coefficient in the visible/near infrared region of the electromagnetic spectrum (i.e. in the region of 400 nm to 3000 nm, e.g. in the region of 400 nm to 2500 nm) of less than 40 mm$^{-1}$, e.g. less than 20 mm$^{-1}$, or less than 10 mm$^{-1}$.

Preferably, the weakly scattering black pigment is carbon black. Other weakly scattering black pigments may include bone black (10% carbon black+84% calcium phosphate), copper chromite black ($CuCr_2O_4$), synthetic iron oxide black ($Fe_3O_4$ magnetite) and perylene black.

Preferably the absorption coefficient of the weakly scattering black pigment is determined at least over a wavelength in the range 300 to 2500 nm.

Preferably, step (iii) comprises taking measurements of the collimated and diffused transmission spectrum. This is advantageous as it allows one to verify that the absorption coefficient can be approximated by the measured extinction coefficient. In particular, step (iii) involves taking a plurality of measurements of the transmission spectrum at different volume fractions at which there is a linear relationship the amount of scattering and volume fraction.

Preferably the reflectance spectrum and the further reflectance spectrum are obtained using an optically thick layer of the mixture.

Preferably, the method includes the step of
v) combining the reflectance spectrum and further reflectance spectrum and calculating the Kubelka Munk absorption and scattering coefficients for the scattering coloured pigment as a function of scattering coloured pigment volume fraction and wavelength.

This is advantageous as the reflectance spectrum provides an accurate characterisation of the scattering coloured pigment, which results in accurate Kubelka Munk absorption and scattering coefficients, particularly in the near infrared part of the spectrum.

Preferably the method includes the step of
vi) determining the scattering coloured pigment volume fraction required to spectrally match a target reflection spectrum using the coefficients calculated in step (v).

Thus, the method comprises a colour matching method that can accurately match a target colour. This method is advantageous as the colour match can be performed more accurately as the scattering coloured pigment can be reliably characterised over a wide range of wavelengths. Further, the method allows the large particle size scattering coloured pigment volume fraction required to achieve a colour match to be determined prior to preparing the pigment mixture.

Accordingly, the method may include the step of
(vii) programming a metering apparatus to prepare a formulation in accordance with the volume fraction calculated.

Preferably, steps (i), (iv) and (v) are repeated for different coloured pigments & step (vi) comprises determining the volume fraction of each coloured pigment to match the target colour.

Preferably, the reflectance spectra are obtained with a resolution of substantially 10 nm.

Preferably, the method includes the step of calculating the total solar reflectance of the coloured pigment at the volume fraction determined to match the target colour, as a function of film thickness. Preferably method includes the step of calculating the total solar reflectance over at least part of the visible spectrum and infra-red spectrum. In particular, over the wavelength range 300 to 2500 nm.

According to a second aspect of the invention we provide a pigment characterisation system adapted to perform the method of the first aspect of the invention to characterise a scattering coloured pigment.

Preferably, the system includes a target colour matching element adapted to control a metering device, the target colour matching element adapted to use the characterisation information of the scattering coloured pigment to determine the volume fraction required to match a target colour, the target colour matching element also being adapted to control the metering device to create a coloured substance that matches the target colour.

Preferably, the system includes a comparator adapted to measure the spectral properties of the coloured substance and compare them with the target colour and, if a match is not detected within predetermined bounds, adjust the concentration of the coloured pigment to obtain a closer match.

Preferably, the system includes a total solar reflectance calculator adapted to calculate the total solar reflectance over at least part of the visible spectrum and infra-red spectrum using the reflectance spectrum. In particular, the total solar reflectance calculator is adapted to calculate over the wavelength range 300 to 2500 nm. This is advantageous as the total solar reflectance calculator can accurately predict how a paint will behave in sunlight. This is particularly useful for cool coloured paints.

There now follows by way of example only a detailed description of the present invention with reference to the accompanying drawings in which:

DETAILED DESCRIPTION OF THE DRAWINGS

This invention relates to a method for colour matching a target colour by determining the required volume fraction or concentration of a colour pigment. Further, the method allows an apparatus to accurately replicate colours without the need to iteratively adjust concentrations to arrive at the correct colour match. This is particularly useful in the field of paint manufacture where it is advantageous to be able to accurately match a selection of pigments to a target colour. In particular, the method disclosed herein is an important pre-production step and can therefore reduce wastage of time and materials.

The method allows selected pigments to be characterised so that they can be accurately metered to form a paint or plastic with a binder having an accurate colour match with a desired target colour. The paints and plastics typically comprise large crystal titanium dioxide and large crystal scattering coloured pigment, such as CICP. The accuracy is achieved by characterising a coloured pigment mixed with a weakly scattering black pigment of known absorption coefficient and characterising the coloured pigment mixed with a large crystal size non-absorbing scattering pigment of known scattering coefficient to obtain scattering and absorption coefficients of the coloured pigment.

Figure 1:
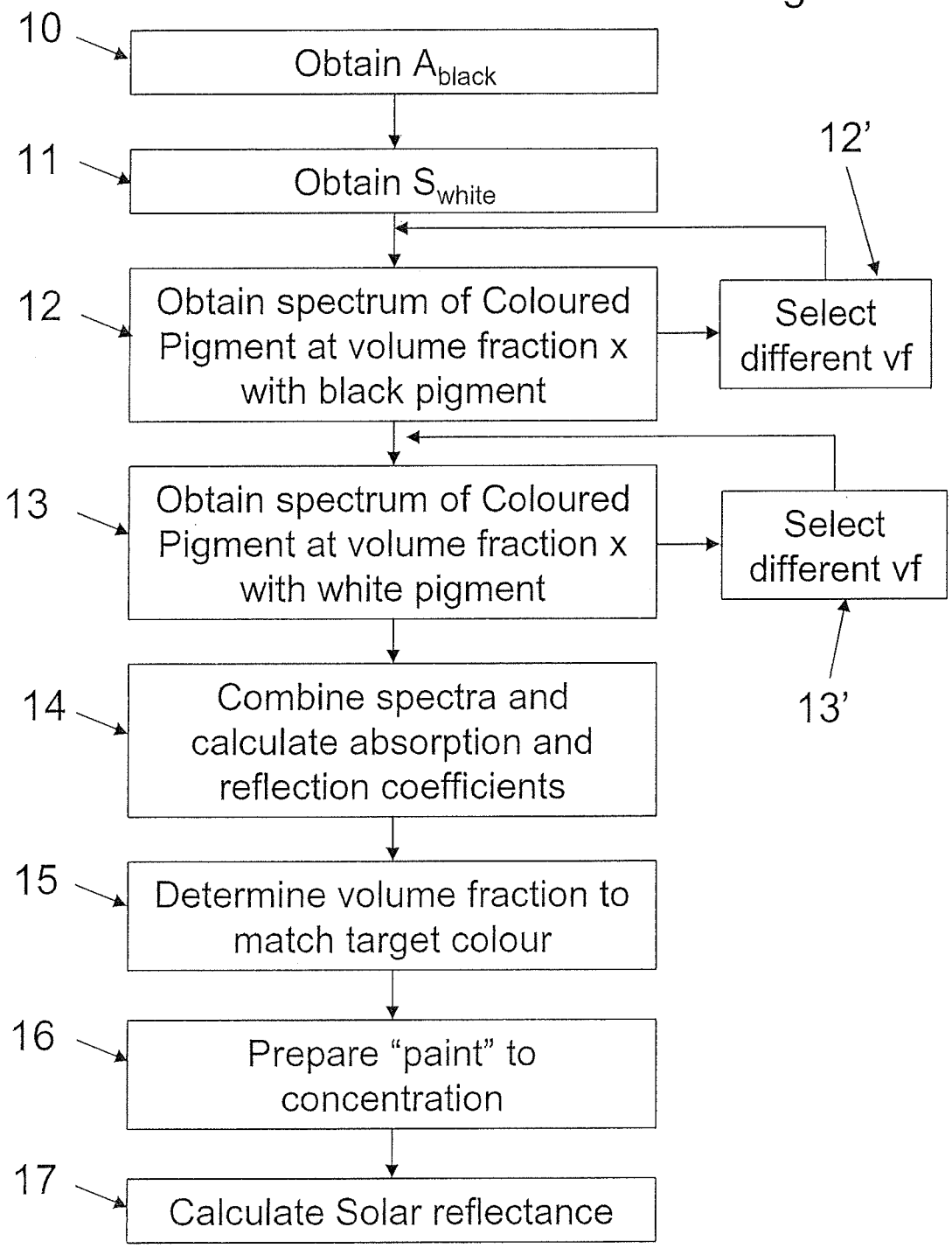
FIG. 1 shows a flow chart illustrating a first embodiment of the method of the first aspect of the invention.

With reference to FIG. 1, step 10 shows the step of obtaining an absorption coefficient of the weakly scattering black pigment as a function of wavelength. In particular, the absorption coefficient is the Kubelka Munk absorption coefficient. The absorption coefficient may already have been determined for the selected black pigment, or it may need to be derived using the following process.

The weakly scattering black pigment, which in this example is carbon black, is prepared by forming a black tinter concentrate. The concentrate is formed by weighing 350 g of 60% Synocryl 826S, 20 g xylene and 40 g Disperbyk 163 into a 1 liter paint can. Then, 40 g of carbon black pigment is added and 2000 g of 6 mm steel beads, such as those sold under the name Ballotini by Potters Industries Inc, to assist dispersion. The lid of the can is secured with clips and adhesive plastic tape. The mixture is then shaken to ensure the components are fully dispersed. This may be achieved using a shaker, such as a "Red Devil" shaker of the Red Devil Equipment Company, for a total of 60 minutes. The black tinter concentrate is then poured off the metal beads and weighed directly into a resin solution as described in more detail below.

The black paint is prepared by weighing 72 g of the black tinter concentrate and 779.2 g of 60% Synocryl 826S into a suitable paint can. The lid is secured and the can is shaken, and trundled, for a minimum of 2 hours or until the paint is homogeneous.

The paint is then applied to a substrate. First, a sheet of Melinex® film (manufactured by DuPont) is degreased by rubbing over with acetone and is then placed on a rubber impression bed. A pool of paint is placed on the top part of the film and drawn down with a No. 9 wire-wound applicator using a smooth action, and allowed to fully dry or to be stoved at an appropriate temperature. The above procedure is repeated using No. 3 and 0 applicators. Thus, we obtain three samples of differing film thicknesses. The film thickness can be calculated as follows. After drying is complete the samples are cut to give a convenient size sample of known area, this sample is weighed and the panels are then ready for their transmission measurements to be taken. After making the transmission measurement as described below, the paint film is removed with acetone. The squares of Melinex are then reweighed, and by subtraction from the original weight, the weight of paint film is determined. Using this film weight and the specific gravity of the dry paint film and the sample area, the film thickness is calculated.

Figure 2:
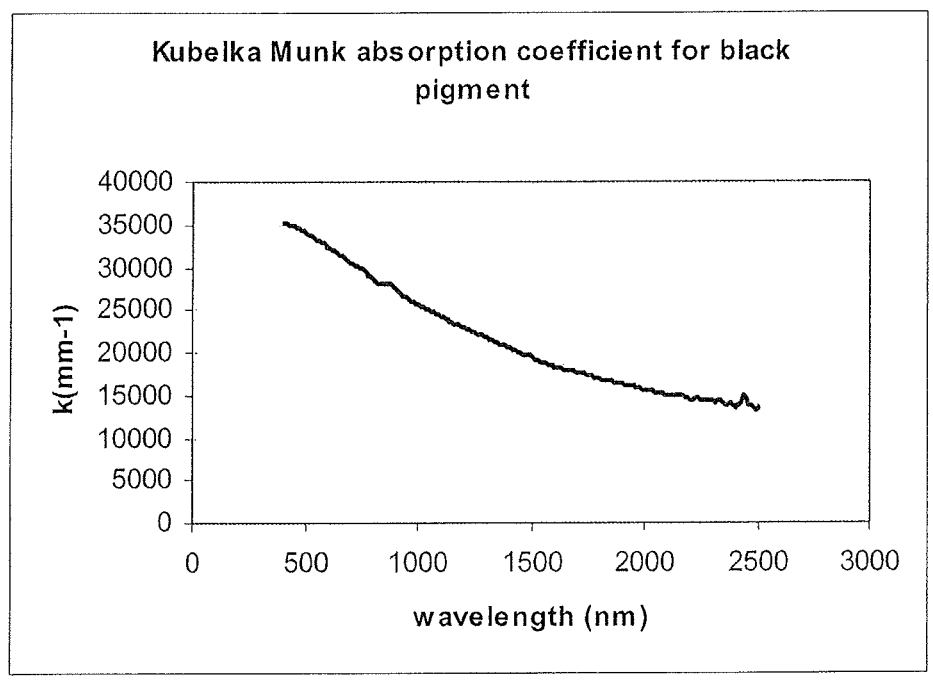
FIG. 2 shows a graph of absorption coefficient vs. wavelength for a black pigment.

The collimated and diffuse transmission spectra are recorded at a resolution of 10 nm over a range of frequencies covering the ultraviolet, visible spectrum and infra-red regions, namely from approximately 300 to 2500 nm. An appropriate spectrometer is a Cary 5000 UV-VIS-NIR spectrometer manufactured by Varian Inc. Each of the three samples is measured to obtain readings for different thicknesses. FIG. 2 shows an example of the spectrum obtained.

The transmission spectra for the collimated and diffuse transmission measurements are then compared to ensure that the contribution of pigment scattering to the measured extinction is minimal. If so, it can be assumed that the absorption coefficients can be approximated by the extinction coefficients. If comparisons between the collimated and diffuse transmission measurements reveal a significant discrepancy between absorption and extinction coefficients, a different, less scattering black pigment is selected.

The Kubelka Munk absorption coefficient for the black pigment can then be calculated from the percentage transmission measurements (% Transmission) obtained above, using the following equation:

$$\text{Absorbance} = \ln\left(\frac{1}{\% \text{ Transmission}/100}\right) \quad (1)$$

The pigment's Kubelka Munk absorption coefficient, $A_{black}$, is then calculated from the Transport Absorption Coefficient (TAC) obtained from the Absorbance, the film thickness T and the black pigment volume fraction $V_{black}$ using the following equation, $$TAC = \frac{\text{Absorbance}}{T \times V_{black}} \quad (2)$$

and $$A_{black} = 2 \times TAC \quad (3)$$

This procedure can be repeated for formulations containing different volume fractions of the black pigments to check for linearity between absorption and volume fraction. For example, for carbon black, volume fractions of 0.01, 0.005 and 0.001 may be used.

Step 11 shows the step of obtaining the Kubelka Munk absorption coefficient for a substantially non-absorbing scattering pigment. The coefficient may be predetermined, although it can be obtained by the following method.

The calculation of a non-absorbing scattering pigment's Kubelka Munk scattering coefficient as a function of wavelength and non-absorbing pigment volume fraction requires the preparation of a set grey paints containing a substantially non-absorbing scattering pigment at a range of volume fractions with a fixed volume fraction of the black pigment.

Calculations are performed to determine the masses of black pigment, prepared as a paint as described above, and the masses of non-absorbing scattering pigment, which need to be mixed to give a set of grey paints with volume fractions of non-absorbing scattering pigment of 0.05, 0.1, 0.15, 0.2, 0.25, 0.3, 0.35 and 0.4.

The required masses of black pigment and non-absorbing scattering pigment are weighed out for each grey paint. The required combinations are mixed. Any high speed dispersive mixer, for use in the paint industry, may be used. The grey paint is now ready for application to a substrate.

A pool of each grey paint is placed on an opacity chart and drawn down with a No. 9 wire-wound applicator using a smooth action. It is then allowed to fully dry or is stoved at an appropriate temperature.

The percentage reflection is recorded at a resolution of substantially 10 nm from 300 to 2500 nm using a spectrometer. As mentioned above, a Cary 5000 UV/Vis/NIR spectrometer fitted with a 150 mm diameter integrating sphere, or any similar apparatus, is appropriate. Measurements are made over the black and over the white portions of the opacity chart. The spectra over the black regions and over the white regions are compared to ensure that the paint film is optically thick throughout the wavelength range. Thus, if no difference in the spectra over the black and white regions is detected, the paint layer is "optically thick". If a difference is detected, the thickness of the layer is increased until no difference is detected. Thus, a film that is optically thick has a reflectance spectrum that is the same when measured over a black and white substrate.

The measurements are repeated for the range of non-absorbing scattering pigment volume fractions to characterise the effect of crowding on scattering.

The calculation of the ratio between the Kubelka Munk scattering coefficient and the absorption coefficient can be made from the percentage reflectance measured from the spectrum.

The first step in this calculation is to use Saunderson's equation to correct the measured percentage reflection (% reflection) for boundary effects.

$$R_{corr} = \frac{(\% \text{ Reflection}/100) - 0.05}{(1 - 0.05 - 0.55 \times (1 - (\% \text{ Reflection}/100))} \quad (4)$$

The ratio of the Kubelka Munk absorption to Kubelka Munk scattering coefficients for the grey paint $(K/S)_g$ is then calculated from the corrected percentage reflection $R_{corr}$.

$$\left(\frac{K}{S}\right)_g = \frac{(R_{corr} - 1)^2}{2 \times R_{corr}} \quad (5)$$

The volume fraction in the dry paint film $(\phi_b)$ and absorption coefficient are known for the black pigment. We can assume that the absorption is dominated by the absorption of the black pigment in the wavelength range 410-2500 nm and therefore we can approximate the Kubelka Munk absorption coefficient of the grey mixture $K_g$ by $$K_g = k_b \times \phi_b \quad (6)$$

where $k_b$ is the Kubelka Munk absorption coefficient of the black pigment. We can assume this range because the substantially non-absorbing scattering pigment i.e. $TiO_2$ is strongly absorbing (i.e. 'black') below 400 nm so carbon black no longer dominates. Thus, the scattering coefficient $S_g$ is given by:

$$S_g = \left(\frac{S}{K}\right)_g \times k_b \times \varphi_b \quad (7)$$

$S_g$ is calculated for a set of wavelengths and volume fractions of the non-absorbing pigment $\phi_{nas}$. At each wavelength the dependence of $S_g$ on $\phi_{nas}$ was fitted to a polynomial of the third degree.

$$S_g(\phi_{nas},\lambda) = \alpha_1(\lambda)\phi_{nas} + \alpha_2(\lambda)\phi_{nas}^2 \alpha_3(\lambda)\phi_{nas}^3 \quad (8)$$

The data set also allows identification of the non-absorbing pigment volume fraction in the dry paint film below which the approximation $$S_g = s_{nas} \times \phi_{nas} \quad (9)$$

is valid throughout the wavelength range 410-2500 nm.

The volume fraction dependence of the Kubelka Munk scattering coefficient being fitted to the polynomial allows the scattering function to be interpolated for any pigment volume fraction.

In order to calculate the Kubelka Munk scattering and absorption coefficient reflectance measurements are made in paint films in which the coloured pigment to be characterised is incorporated into both black and white paints.

Step 12 comprises obtaining the spectrum of a scattering coloured pigment at a range of volume fractions with the black pigment.

This step comprises the preparation of a set of paints containing both the black pigment at a predetermined volume fraction and the coloured pigment at a range of volume fractions For easily dispersable pigments, the pigment can be added to a binder in a mixer pot as a powder. For coloured pigments which are more difficult to disperse, a tinter concentrate is first produced and shaken following the method described above for the black pigment. The required mass of tinter concentrate is then added to the binder in the mixer pot.

The masses of the black paint (preparation detailed above) and the coloured pigment which need to be mixed to give a set of paints with volume fractions of coloured pigment of 0.01, 0.02, 0.05 and 0.07 are calculated. A person skilled in the art will be familiar with this calculation. The volume fractions have been chosen to ensure that the measured scattering coefficients will be linear in pigment volume fraction, as will be known or determined during the absorbance measurements.

For each paint the amount of coloured pigment and black paint is weighed and added to a pot and then mixed for approximately 2.5 minutes, using a suitable dispersion apparatus (for example a high speed disperser). Then an additional remaining quantity of black paint is added and the mixture is mixed further (approximately 2 minutes, for example). The paint is now ready for application.

A pool of paint is placed on the top part of an opacity chart and drawn down with the No. 9 wire-wound applicator using a smooth action, and allowed to fully dry or stoved at an appropriate temperature.

The percentage reflection is recorded at 10 nm intervals from 300 to 2500 nm using a spectrometer such as a Cary 5000 UV/Vis/NIR spectrometer fitted with a 150 mm diameter integrating sphere. Measurements are made over the black and over white portions of the opacity chart. The spectra over black and over white are compared to ensure that the paint film is optically thick throughout the wavelength range. If a difference in the spectra is detected the thickness of the paint is increased until there is no difference. The paint is then deemed "optically thick" and the spectrum is measured and recorded.

Step 12' shows the selection of a different volume fraction and the repetition of step 12 until all of the volume fractions have been processed.

Step 13 comprises obtaining the spectrum of the coloured pigment at a range of volume fractions with the non-absorbing, scattering pigment.

This step comprises the preparation of a set of paints containing both the non-absorbing, scattering pigment at known volume fraction and the coloured pigment at a range of volume fractions For easily dispersable coloured pigments, the pigment can be added to a binder mixture in a mixer pot as a powder. For coloured pigments which are more difficult to disperse, a tinter concentrate is first produced and shaken following the method described above for the black pigment. The required mass of tinter concentrate is then added to the binder in the mixer pot.

The masses of the non-absorbing scattering pigment (preparation detailed above) and the coloured pigment, which need to be mixed to give a set of paints with volume fractions of non-absorbing scattering pigments of 0.15 in the dry paint film and coloured pigment volume fractions of 0.01, 0.02, 0.05 and 0.07 in the dry paint film are calculated. These volume fractions have been chosen to ensure that the measured scattering coefficients will be linear in pigment volume fraction, as will be known or determined during the absorbance measurements.

For each paint, the amount of coloured pigment and non-absorbing scattering pigment is weighed and added to a mixer pot and dispersed for approximately 2.5 minutes. Then, an additional quantity of resin is added and the mixture is mixed further. For example, for a further 2 minutes. The paint is now ready for application.

A pool of paint is placed on the top part of an opacity chart and drawn down with the No. 150 wire-wound applicator using a smooth action, and allowed to fully dry or stoved at an appropriate temperature. This procedure is repeated several times (in this embodiment three times) to produce a film with a film thickness of about 200 microns, which has been found to be optically thick.

The percentage reflection is recorded at 10 nm intervals from 300 to 2500 nm using a Cary 5000 UV/Vis/NIR spectrometer fitted with a 150 mm diameter integrating sphere. Measurements are made over the black and over white portions of the opacity chart. The spectra over black and over white are compared to ensure that the paint film is optically thick throughout the wavelength range. If a difference in the spectra is detected, the thickness of the paint is increased until there is no difference. The paint is then deemed "optically thick" and the spectrum is measured and recorded.

Step 13' shows the selection of a different volume fraction and the repetition of step 13 until all of the volume fractions have been processed.

Step 14 comprises combining the reflection spectrum obtained in steps 12 and 13 and using the Kubelka Munk equations to create a set of simultaneous equations. The solution of these equations allows the determination of the Kubelka Munk absorption and scattering coefficients for the pigments as a function of pigment volume fraction and wavelength.

The first step is to calculate a ratio between the Kubelka Munk scattering and absorption coefficient from the percentage reflection (% Reflection).

To achieve this it is necessary to use Saunderson's equation to correct the measured percentage reflection for boundary effects. The corrected percentage reflection, $R_{corr}$, is calculated as follows:

$$R_{corr} = \frac{(\% \text{ Reflection}/100) - 0.05}{(1 - 0.05 - 0.55 \times (1 - (\% \text{ Reflection}/100)))} \quad (9)$$

The ratio of the Kubelka Munk absorption coefficient to the Kubelka Munk scattering coefficients for the grey paint $(K/S)_g$ can then be calculated from the corrected fractional reflection.

$$\left(\frac{K}{S}\right) = \frac{(R_{corr} - 1)^2}{2 \times R_{corr}} \quad (10)$$

Using the methodology described above we can calculate the ratios of Kubelka Munk scattering and absorption coefficients for coloured pigments in both black and white paints —$(K/S)_{c,b}$ and $(K/S)_{c,w}$ respectively, for a range of coloured pigment volume fractions. The volume fractions of the black ($\phi_b$), non-absorbing scattering ($\phi_{nas}$) and coloured pigments ($\phi_c$) in the dry paint films have been found. The absorption coefficient of the black pigment ($k_b$) and the scattering coefficient of the non-absorbing scattering pigment ($s_{nas}$) have also been obtained. The Kubelka Munk scattering and absorption coefficients ($s_c$ and $k_c$) for the coloured pigments can now be calculated (in the regions where the dependence on coloured pigment volume fraction is linear) using the following equations.

$$s_c \varphi_c = \frac{s_{nas}\varphi_{nas} \times \left(\frac{K}{S}\right)_{c,w} + k_b \varphi_b}{\left[\left(\frac{K}{S}\right)_{c,b} - \left(\frac{K}{S}\right)_{c,w}\right]} \quad (11)$$

$$k_c \varphi_c = \left(\frac{K}{S}\right)_{c,w} \times (s_{nas}\varphi_{nas} + s_c\varphi_c) \quad (12)$$

$s_c$ and $k_c$ are obtained by taking the slopes of plots of $s_c\phi_c$ and $k_c\phi_c$, calculated from the above equations, against $\phi_c$.

Step 15 comprises calculating the pigment concentrations required to spectrally match a target reflection in the visible part of the spectrum.

First, the range of concentrations over which the assumption of linearity can be applied when combining pigments is determined. This may be predetermined or derived from the measurements of the coloured pigment in carbon black.

The calculation of a paint formulation that will match a desired target colour is determined as follows.

The percentage reflection of an object with the desired target colour is measured every 10 nm over the visible spectrum, such as between 400 and 770 nm using a Cary 5000 UV/Vis/NIR spectrometer fitted with a 150 mm diameter integrating sphere. Alternatively a target colour may be obtained by way of a set of parameters.

The predicted percentage reflection for a paint film containing a given mixture of pigments is calculated from the corrected percentage reflection ($R_{corr}$) for a paint film containing a given mixture of pigments using the following equation.

$$\% \text{ Reflection} = \left[\frac{(0.05 + ((1 - 0.05) \times (1 - 0.5) \times R_{corr})}{(1 - 0.5 \times R_{corr})}\right] \times 100 \quad (13)$$

The corrected fractional reflection can be calculated from the ratio of the Kubelka Munk scattering and absorption coefficients for an optically thick film containing a given mixture of pigments using the following equation.

$$R_{corr} = 1 + \left(\frac{K}{S}\right) - \left(\left(1 + \left(\frac{K}{S}\right)\right)^2 - 1\right)^{1/2} \quad (14)$$

The ratio of the Kubelka Munk scattering and absorption coefficients for an optically infinitely thick film containing a given mixture of pigments can be calculated from their volume fractions in the dry paint film and their Kubelka Munk absorption and scattering coefficients using the following equation $$\left(\frac{K}{S}\right) = \frac{k_1 \times \varphi_1 + k_2 \times \varphi_2 + k_3 \times \varphi_3 \ldots}{s_1 \times \varphi_1 + s_2 \times \varphi_2 + s_3 \times \varphi_3 \ldots} \quad (15)$$

Where $k_n$ is the absorption coefficient of pigment n, $s_n$ is the scattering coefficient of pigment n and $\phi_n$ is the volume fraction of pigment n in the dry paint film.

The above calculations can be repeated to give a predicted percentage reflection at 10 nm intervals in the wavelength range 400 to 770 nm for an optically infinitely thick film containing a given mixture of pigments.

The values of the volume fractions of the various pigments in the dry paint film can be adjusted until the sum of the squared differences between the predicted percentage reflections and the target percentage reflections measured at 10 nm intervals between 400 and 770 nm reaches a minimum value.

A paint metering system can then be programmed to produce a paint with the required pigment volume fractions in the dry paint film, and thus to match the desired colour Step 16 represents a paint being prepared to the calculated formulation.

Step 17 defines the step of calculating the solar reflectance of the formulation. This is achieved as follows:

The predicted percentage total solar reflection for a paint film containing a given mixture of pigments is calculated from the percentage reflection predicted at 10 nm intervals between 300 and 2500 nm, using the following equation $$\% \text{ Total solar reflection} = \frac{\sum_{300}^{2500} \text{Solar Irradiance}(\lambda) \times (\% \text{ Reflection}(\lambda)/100)}{\sum_{300}^{2500} \text{Solar Irradiance}(\lambda)} \quad (16)$$

The Solar Irradiance is a predetermined function of wavelength that represents the sun's radiation emission. The percentage reflection, % Reflection, is calculated from the corrected fractional reflection ($R_{corr}$) for a paint film containing a given mixture of pigments using the following equation.

$$\% \text{ Reflection} = \left[\frac{(0.05 + ((1 - 0.05) \times (1 - 0.5) \times R_{corr})}{(1 - 0.5 \times R_{corr})}\right] \times 100 \quad (17)$$

The corrected fractional reflection can be calculated from the ratio of the Kubelka Munk scattering and absorption coefficients for an optically infinitely thick film containing a given mixture of pigments using the following equation:

$$R_{corr} = 1 + \left(\frac{K}{S}\right) - \left(\left(1 + \left(\frac{K}{S}\right)\right)^2 - 1\right)^{1/2} \quad (18)$$

The ratio of the Kubelka Munk scattering and absorption coefficients for an optically thick film containing a given mixture of pigments can be calculated from their volume fractions in the dry paint film and their Kubelka Munk absorption and scattering coefficients using the following equation:

$$\left(\frac{K}{S}\right) = \frac{k_1 \times \varphi_1 + k_2 \times \varphi_2 + k_3 \times \varphi_3 \ldots}{s_1 \times \varphi_1 + s_2 \times \varphi_2 + s_3 \times \varphi_3 \ldots} \quad (19)$$

Where $k_n$ is the absorption coefficient of pigment n, $s_n$ is the scattering coefficient of pigment n and $\phi_n$ is the volume fraction of pigment n in the dry paint film. Thus, the total solar reflection of this pigment mixture, as a function of film thickness, over both black and white substrates can be calculated.

This method allows the desired ability to match colours and predict total solar reflections and heat build-ups for a material pigmented with a given set of non scattering or large crystal materials prior to production of the paint. This is advantageous as not only is the colour of the paint accurately matched to the target colour, but the total solar reflection and heat build up of materials containing coloured pigments can be quantitatively predicted. This is particularly useful as it allows the effective development of "cool coloured" materials.

The large crystal sizes of the scattering pigments preferentially used in cool coloured materials allows this methodology to be extended to higher volume fractions than in conventional systems.

The Kubelka Munk approach is traditionally used to determine the visible reflection spectrum of materials containing a mixture of non-scattering coloured pigments in combination with a strongly scattering titanium dioxide pigment (i.e. a non-absorbing scattering pigment). The use of this approach is more problematic at high titanium dioxide volume fractions and when the coloured pigments contribute significantly to the total scattering of the material, due to crowding effects. Predictions are even more difficult in the near infra-red part of the spectrum where the effect of crowding on scattering is even more pronounced.

This approach is particularly applicable for pigments designed for use in cool coloured materials, that is materials having high reflection in the near infra-red part of the spectrum, because the scattering pigments used in cool coloured applications often have a larger crystal size than those used in applications where the reflection of near infra-red radiation is not of any importance. The volume fractions at which pigment crowding becomes important are considerably higher with these larger crystal materials and therefore the approach described above can be applied to a wider range of such formulations than is the case for non cool coloured materials. For example, it has been advantageously found that the linear relationship between scattering coefficient and volume fraction exists below a pigment volume fraction of about 30% when large particle size pigments (approximately 1 micron) are used for characterising, whereas this linear relationship only exists below about a pigment volume fraction of about 10% for a 0.3 micron sized particle.

Figure 3:
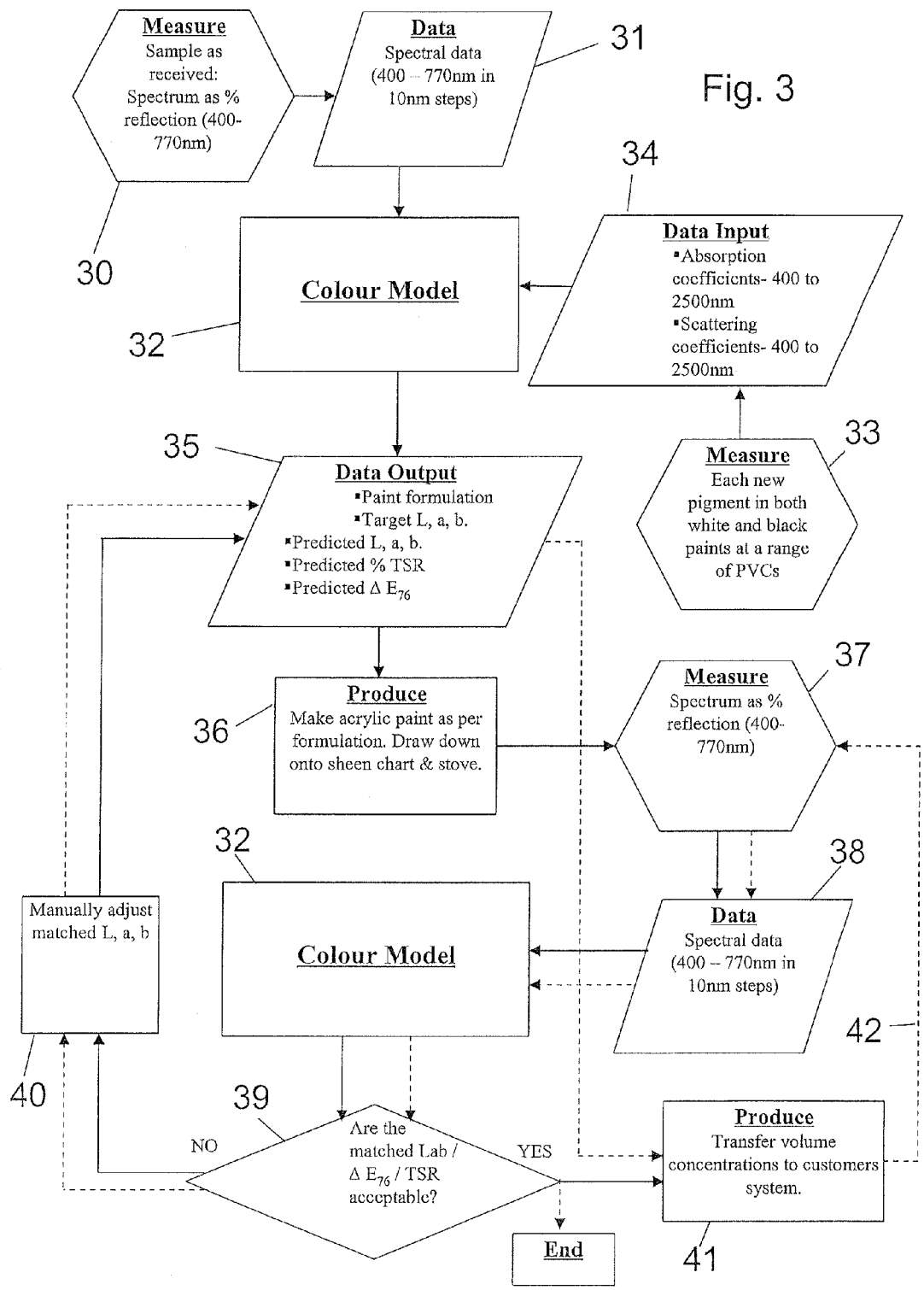
FIG. 3 shows a process diagram illustrating an embodiment of the implementation of the system of the second aspect of the invention.
Figure 4:
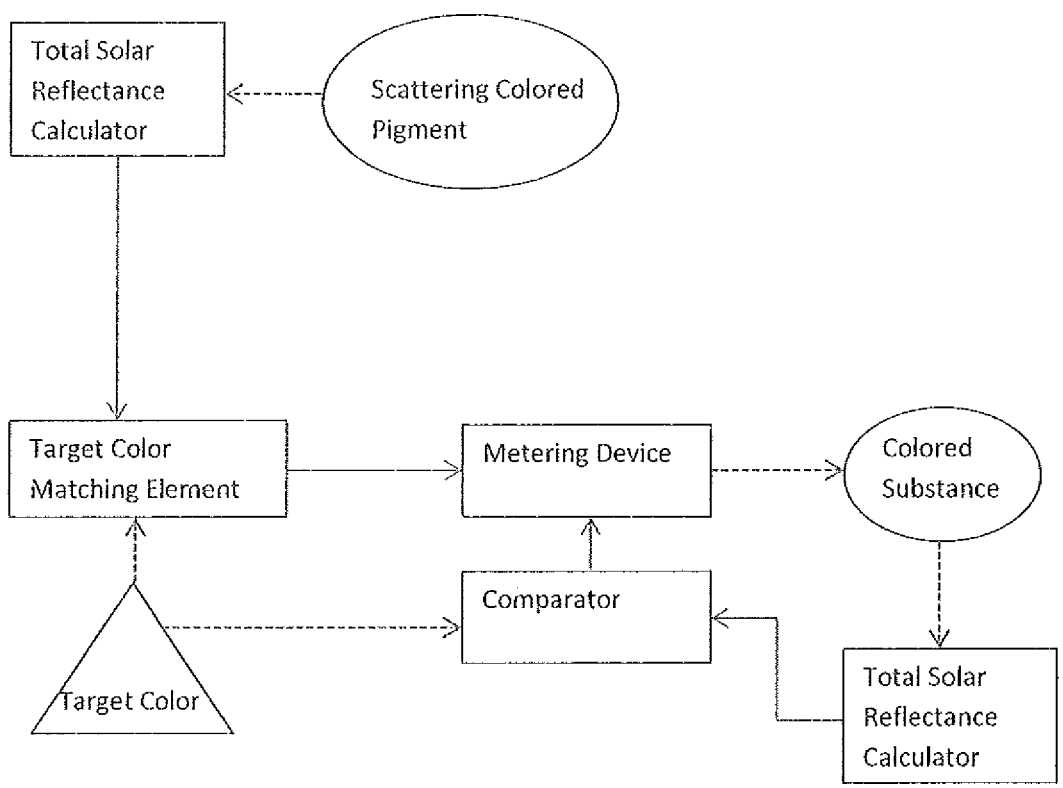
FIG. 4 shows an embodiment of a target color matching element, the metering device, the colored substance, the comparator, and the total solar reflectance calculator.

FIG. 3 shows an industrial process that utilizes an embodiment of the method of the invention. The industrial process is performed by a colour matching system. Step 30 shows the receipt of a sample material, the colour of which it is desired to match with a paint. This colour is the target colour. The reflectance spectrum of the sample is taken in the visible part of the spectrum. In the present example, this is between 400 and 770 nm at a resolution of 10 nm.

The spectral data from the measurements is received at step 31 and forwarded to the colour model calculator 32. The colour model calculator 32 stores the absorption coefficients and the scattering coefficients for a variety of coloured pigments. These coefficients are obtained in accordance with the method described above. In particular, step 33, illustrates the measurement of the spectrum of each pigment as described above. Step 34 shows the compilation of the absorption coefficients and the scattering coefficients for input into the colour model calculator 32.

The colour model calculator 32 determines the combination of colour pigments and their volume fractions in order to achieve a paint of the target colour, as described above.

At step 35, the calculated paint formulation is output from the colour model calculator 32, which comprises the volume fractions of the pigments required in the dry paint film. The output comprises the CIE L*a*b* colour space 1976 coordinates for the matched colour in terms of the lightness L*, and the colour coordinates a* and b*. Further, the calculator 32 generates the target colour L*a*b* colour space L*, a* and b*. The output of the calculator also includes the predicted percentage total solar reflection of the matched colour so that the thermodynamic behaviour of the paint can be assessed. Further, the predicted difference between the colour of the target colour and the colour of the formulation that the calculator determines to be a match of the target colour, $\Delta E_{76}$ is produced. It will be appreciated that the colour matching ability of the system is limited by the colour pigments that are available and therefore the $\Delta E_{76}$ value is an industry standard to show how close the colour match is.

The output from step 35 is used in a pigment metering apparatus that prepares the matched paint at step 36. The composition that is output comprises the masses of all the components of the wet paint calculated from the pigment volume concentrations required in the dry paint film, as determined by the calculator 32. This calculation requires a knowledge of the densities of all the materials present in the wet paint and dry paint film.

As part of a quality control procedure, step 37 involves the measurement of the reflection spectrum for the matched paint. The spectrum is taken over the visible spectrum and, in particular, between 400 and 770 nm at a resolution of 10 nm. The data is collated at step 38 and fed back to the colour model calculator 32 (shown twice in FIG. 3 for clarity). A verification step is performed at step 39 to check how accurate the predicted values were to the paint that was actually produced. This can be used to identify errors in the coefficients obtained in steps 33 and 34 or inaccuracies in the pigment metering apparatus used in step 36.

Step 40 shows the Lab colour space coordinates of the matched colour being adjusted. This may be performed manually, or may be an automated procedure that iteratively adjusts the values to obtain the closest match. A paint can then be produced to the adjusted formulation.

If the predicted Lab colour space values, total solar refection or $\Delta E_{76}$ values are sufficiently accurate, the process may proceed to step 41 in which the paint can go into full production for sending to customers. The dashed line 42 shows that further quality control checks may be made on the customer's systems. For example, the customer's pigment metering apparatus may produce a slightly different colour that can be compensated for by this additional check.

The invention claimed is:

1. A method of characterising a scattering coloured pigment for use in the determination of the absorption and scattering coefficients of the scattering coloured pigment, the method comprising the step of:
   (i) preparing a white paste comprising a mixture of the scattering coloured pigment and a substantially non-absorbing scattering pigment at a plurality of different volume fractions, wherein the scattering coloured pigment is a large particle size pigment having a particle size of greater than 0.6 microns and wherein the substantially non-absorbing scattering pigment is a large particle size titanium dioxide pigment having a particle size greater than 0.6 microns;
   (ii) obtaining a reflectance spectrum, using a spectrometer, at least over wavelengths in the visible spectrum and infrared spectrum of the mixture of the scattering coloured pigment with a substantially non-absorbing scattering pigment at a plurality of different volume fractions; and (iii) obtaining a scattering coefficient of the substantially non-absorbing scattering pigment as a function of volume fraction and wavelength and storing the scattering coefficient in a color model calculator.

2. A method according to claim 1, in which the method includes the step of determining the particle size of the scattering coloured pigment and selecting a non-absorbing scattering pigment having a particle size within 0.5 microns of the particle size of the scattering coloured pigment for performing characterisation therewith provided that the determined particle size is greater than 0.6 microns.

3. A method according to claim 1, in which the scattering coloured pigment is selected from: Complex Inorganic Coloured Pigments; Nickel Antimony Titanate; Chrome Antimony Titanate; Manganese Antimony Titanate; Zinc Iron Chromite Brown Spinel; Chromium Green-Black Hematite; Cobalt Aluminate Blue Spinel; Cobalt Titanate Green Spinel; and Cobalt Chromite Green Spinel.

4. A method according to claim 1, in which the reflectance spectrum of the scattering coloured pigment is determined over a wavelength range of 300 nm to 2500 nm.

5. A method according to claim 1, in which the method includes the steps of:
(iv) obtaining an absorption coefficient of a weakly scattering black pigment as a function of wavelength at a plurality of different volume fractions and storing the absorption coefficient in the color model calculator; and
(v) obtaining a further reflectance spectrum of a mixture of the scattering coloured pigment with the black pigment at a plurality of different volume fractions.

6. A method according to claim 5, in which the weakly scattering black pigment is carbon black.

7. A method according to claim 5, in which the reflectance spectrum and the further reflectance spectrum are obtained using an optically thick layer of the mixture.

8. A method according to claim 5, in which the method includes the step of:
(vi) combining the reflectance spectrum and further reflectance spectrum and calculating the Kubelka Munk absorption and scattering coefficients for the scattering coloured pigment as a function of scattering coloured pigment volume fraction and wavelength and storing the calculated Kubelka Munk absorption and scattering coefficients in the color model calculator.

9. A method according to claim 8, in which the method includes the step of:
(vii) determining the scattering coloured pigment volume fraction required to spectrally match a target reflection spectrum using the coefficients calculated in step (vi).

10. A method according to claim 8, in which the method includes the step of:
(viii) programming a metering apparatus to prepare a formulation in accordance with the volume fraction calculated.

11. A method according to claim 9, in which steps (ii), (v), and (vi) are repeated for different coloured pigments and step (vii) comprises determining the volume fraction of each coloured pigment to match the target colour.

12. A method according to claim 1, in which the reflectance spectra are obtained with a resolution of substantially 10 nm.

13. A method according to claim 8, in which the method includes the step of calculating the total solar reflectance of the coloured pigment at the volume fraction determined to match the target colour, as a function of film thickness.

14. A method according to claim 13, in which the method includes the step of calculating the total solar reflectance over at least part of the visible spectrum and infrared spectrum.

15. A method according to claim 14, in which the method includes the step of calculating the total solar reflectance over the wavelength range 300 to 2500 nm.

16. A pigment characterisation system adapted to perform the method of claim 1 to characterise a scattering coloured pigment.

17. A pigment characterisation system according to claim 16, in which the system includes a target colour matching element adapted to control a metering device, the target colour matching element adapted to use the characterisation information of the scattering coloured pigment to determine the volume fraction required to match a target colour, the target colour matching element also being adapted to control the metering device to create a coloured substance that matches the target colour.

18. A pigment characterisation system according to claim 16, in which the system includes a comparator adapted to measure the spectral properties of the coloured substance and compare them with the target colour and, if a match is not detected within predetermined bounds, adjust the concentration of the coloured pigment to obtain a closer match.

* * * * *